(12) United States Patent
Yoshida et al.

(10) Patent No.: US 8,779,119 B2
(45) Date of Patent: Jul. 15, 2014

(54) METAL SALT OF CROSSLINKED CELLULOSE DERIVATIVE

(75) Inventors: Naoyuki Yoshida, Chiba (JP); Kazushi Ishida, Chiba (JP); Shuji Sasaki, Chiba (JP); Ippei Yamaoka, Tokushima (JP)

(73) Assignee: JNC Corporation, Tokyo (JP)

( * ) Notice: Subject to any disclaimer, the term of this patent is extended or adjusted under 35 U.S.C. 154(b) by 831 days.

(21) Appl. No.: 12/521,524

(22) PCT Filed: Dec. 26, 2007

(86) PCT No.: PCT/JP2007/075028
§ 371 (c)(1),
(2), (4) Date: Jun. 26, 2009

(87) PCT Pub. No.: WO2008/078795
PCT Pub. Date: Jul. 3, 2008

(65) Prior Publication Data
US 2010/0317844 A1    Dec. 16, 2010

(30) Foreign Application Priority Data
Dec. 26, 2006   (JP) ................................. 2006-349296

(51) Int. Cl.
*C08B 5/14*       (2006.01)
*C08B 11/10*      (2006.01)
*C08B 11/12*      (2006.01)

(52) U.S. Cl.
USPC ..................... 536/59; 536/92; 536/97; 514/57

(58) Field of Classification Search
None
See application file for complete search history.

(56) References Cited

U.S. PATENT DOCUMENTS

| 3,275,576 | A | | 9/1966 | Flodin |
| 3,573,277 | A | * | 3/1971 | Grant .............................. 536/84 |
| 5,108,596 | A | | 4/1992 | Ookuma et al. |
| 5,196,527 | A | | 3/1993 | Ookuma et al. |
| 2003/0027789 | A1 | | 2/2003 | Yamaoka |
| 2005/0220750 | A1 | * | 10/2005 | Robert et al. ................ 424/78.1 |

FOREIGN PATENT DOCUMENTS

| JP | 43-022320 B1 | 9/1968 |
| JP | 61-054451 A | 3/1986 |
| JP | 2-241547 A | 9/1990 |
| JP | 4-161431 A | 6/1992 |
| JP | 10-330401 A | 12/1998 |
| JP | 2003-520302 T | 7/2003 |
| WO | 01/51063 A1 | 7/2001 |
| WO | 01/52911 A2 | 7/2001 |
| WO | 2005/094384 A2 | 10/2005 |

OTHER PUBLICATIONS

Journal of Home Economics of Japan, 1988, pp. 187-195, vol. 39, No. 3.
Ken-Ichiro Arai et al., "Crosslinked Sodium Cellulose Sulfate as Highly Water-Absorbable Material", Sen-i Gakkaishi, 1993, pp. 482-485, vol. 49, No. 9.
J. Pastyr et al., "Preparation and Properties of a Cellulose Sulfate Cation-Exchanger Based on Powdered Cross-Linked Cellulose", Cellulose Chemistry and Technology, 1972, 6, pp. 249-254.
Japanese Patent Office, Office Action issued Feb. 5, 2013, in a counterpart Application No. 2008-551144.

* cited by examiner

*Primary Examiner* — Leigh Maier
(74) *Attorney, Agent, or Firm* — Sughrue Mion, PLLC

(57) ABSTRACT

The invention provides a metal salt of a crosslinked cellulose derivative represented by the following formula (I), wherein the degree of substitution of the hydroxyl group of glucose unit of the crosslinked cellulose derivative by a functional group a is 1 or more.

$$R-O-A \qquad (I)$$

{In the formula (I), R represents a crosslinked cellulose residue and A represents a functional group a having cation-exchange ability.}

1 Claim, 2 Drawing Sheets

METAL SALT OF CROSSLINKED CELLULOSE DERIVATIVE

TECHNICAL FIELD

The invention relates to a metal salt of a crosslinked cellulose derivative having a specific structure, wherein the degree of substitution of the hydroxyl group of glucose unit of the crosslinked cellulose derivative by a functional group a falls within a specific range.

BACKGROUND ART

According to the Results of National Nutrition Survey published by Ministry of Health and Welfare, the common salt intake by a Japanese per day on and after Showa 50 (1975) was 11.5 g or more and particularly, the amount was 12.8 g in Heisei 5 (1993). On the other hand, since there is a correlation between the common salt intake per day and the incidence rate of hypertension, Ministry of Health and Welfare has recommended to control the common salt intake per day to be 10 g or less in order to prevent the incidence of hypertension and further the incidence of cerebral strokes. Also, in the United States, the common salt intake per day is restricted as in Japan and a draft of advice of US Joint Committee has proposed controlling the common salt intake ingested by a hypertension patient per day to be 6 g or less.

Moreover, it is said that there is also a correlation between the common salt intake and the mortality owing to stomach cancer. There is obtained data that the mortality owing to stomach cancer is high in the areas where the common salt intake is large, such as Toyama city and Hirosaki city, while the mortality owing to stomach cancer is low in the areas where the common salt intake is small, such as Beppu city and Okinawa city.

Although it is reported that dietary fiber such as alginate salt has a certain degree of sodium ion adsorption ability (Non-Patent Document 1), the adsorption ability is not yet sufficiently satisfactory.

Since excessive existence of common salt in the body as above adversely affects the human body, it has been desired to develop a new technology which effectively inhibits the absorption of common salt into the body and excretes excessively existing common salt outside the body.

As such a technology, metal salts of cellulose derivatives with metals other than sodium have been proposed (Patent Document 1).

On the other hand, as a technology for altering the properties of cellulose, substituent introduction such as esterification of cellulose and crosslinking of cellulose have been performed.

For example, in aforementioned Patent Document 1, a technology of introducing a functional group having cation-exchange ability as a substituent is proposed.

With regard to the crosslinking of cellulose, depending on the types of the crosslinking agent, methods for introducing the same (reaction conditions) and chemical structures thereof are diversified. However, generally, most of the methods utilize as a functional group the hydroxyl group at 6-position of the glucose skeleton which is a monomer unit. The most commonly known one is a compound having a glycerol skeleton or a 1,2-diol skeleton in the crosslinking structure.

Moreover, as a technology for modifying the water-holding property of cellulose, a technology of introducing a sulfate group and subsequently crosslinking the obtained cellulose sulfate is proposed (Non-Patent Document 2, Patent Document 2).

It is considered that the improvement of performance through the modification of cellulose depends on the crosslinking and the amount of the functional group introduced. However, since both of the crosslinking of cellulose and the introduction of the functional group are conducted to the three hydroxyl groups contained in the glucose unit of celluloses, it is difficult to increase the degree of substitution by the functional group in crosslinked cellulose derivatives having the functional group. Actually, it is very difficult to increase the degree of substitution to be a value exceeding 1.1. Particularly, in the case of introducing the functional group into a crosslinked cellulose, it becomes more difficult to increase the degree of substitution.

In this connection, as a technology for introducing a functional group into a crosslinked cellulose, a technology of reacting the cellulose with $HClO_3S$ in pyridine is reported (Non-Patent Document 3).

Patent Document 1: WO 01/051063
Patent Document 2: JP-T-2003-520302
Non-Patent Document 1: Journal of Home Economics of Japan, 1988, Vol. 39, No. 3, p. 187-195
Non-Patent Document 2: Ken-ichiro Arai, Hideki Gota, "Crosslinked Sodium Cellulose Sulfate as Highly Water-Absorbable Material", SEN-I GAKKAISHI, 1993, Vol. 49, No. 9, p. 482-485
Non-Patent Document 3: J. PASTYR, L. KUNIAK, "PREPARATION AND PROPERTIES OF A CELLULOSE SULFATE CATION-EXCHANGER BASED ON POWDERED CROSS-LINKED CELLULOSE", CELLULOSE CHEMISTRY AND TECHNOLOGY, 1972, 6, P. 249-254

DISCLOSURE OF THE INVENTION

Problems to be Solved by the Invention

However, in the technology of Patent Document 1, it has been found that a tendency to bleed is observed owing to a disorder of the digestive tract, particularly hurting of the intestinal wall and, as a result, extreme anemia is induced in some cases.

On the other hand, even in any of the above technologies, the degree of substitution of the functional group is not sufficiently increased in the crosslinked cellulose derivatives having functional groups. In the filed where the derivatives are directly applied to the human body, for example, in the case of utilizing the crosslinked celluloses having functional groups as oral agents, it is requested to have a high performance in a small amount in order to reduce a burden on the human body. Therefore, it is highly desired to make the degree of substitution of the functional groups higher in the crosslinked celluloses having the functional groups.

Therefore, an object of the invention is to provide a metal salt of a crosslinked cellulose derivative having a higher performance and a high degree of substitution. Furthermore, another object of the invention is to provide a sodium absorption inhibitor capable of actively and safely excreting over-consumed common salt outside the body, and preventive and therapeutic agents for diseases caused by overconsumption of common salt or diseases which require restriction of common salt intake, as well as a food therefor.

Means for Solving the Problems

Means for solving the problems of the invention is described below.

[1] A metal salt of a crosslinked cellulose derivative represented by the following formula (I), wherein the degree of substitution of the hydroxyl group of glucose unit of the crosslinked cellulose derivative by a functional group a is 1 or more:

R—O-A (I)

wherein R represents a crosslinked cellulose residue and A represents a functional group a having cation-exchange ability.

[2] The metal salt according to the above [1], wherein the functional group a is selected from the groups represented by the following formulae (II) to (V):

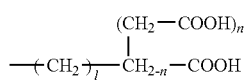 (II)

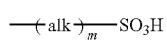 (III)

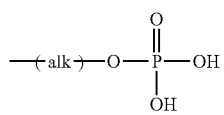 (IV)

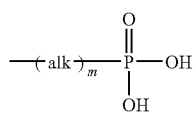 (V)

wherein alk represents an alkylene group having 1 to 6 carbon atoms, 1 represents an integer of 0 to 5, m represents 0 or 1, and n represents an integer of 0 to 2.

[3] The metal salt according to the above [2], wherein the functional group a is selected from the following formulae (II-1), (II-2), (III-1) to (III-5), (IV-1), (V-1), and (V-2):

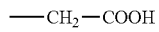 (II-1)

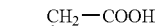 (II-2)

—SO$_3$H (III-1)

—CH$_2$—SO$_3$H (III-2)

—CH$_2$—CH$_2$—SO$_3$H (III-3)

—CH$_2$—CH$_2$—CH$_2$—SO$_3$H (III-4)

—CH$_2$—CH$_2$—CH$_2$—CH$_2$—SO$_3$H (III-5)

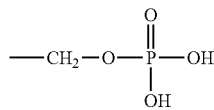 (IV-1)

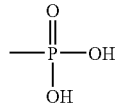 (V-1)

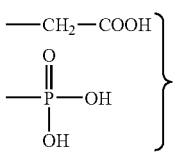 (V-2)

[4] The metal salt according to the above [3], wherein a combination of plurality of the functional groups a is any of the following formulae (c-1) to (c-3):

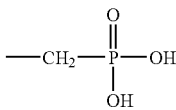 (c-1)

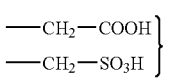 (c-2)

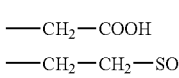 (c-3)

BEST MODE FOR CARRYING OUT THE INVENTION

Metal Salt of Crosslinked Cellulose Derivative

Figure 1:
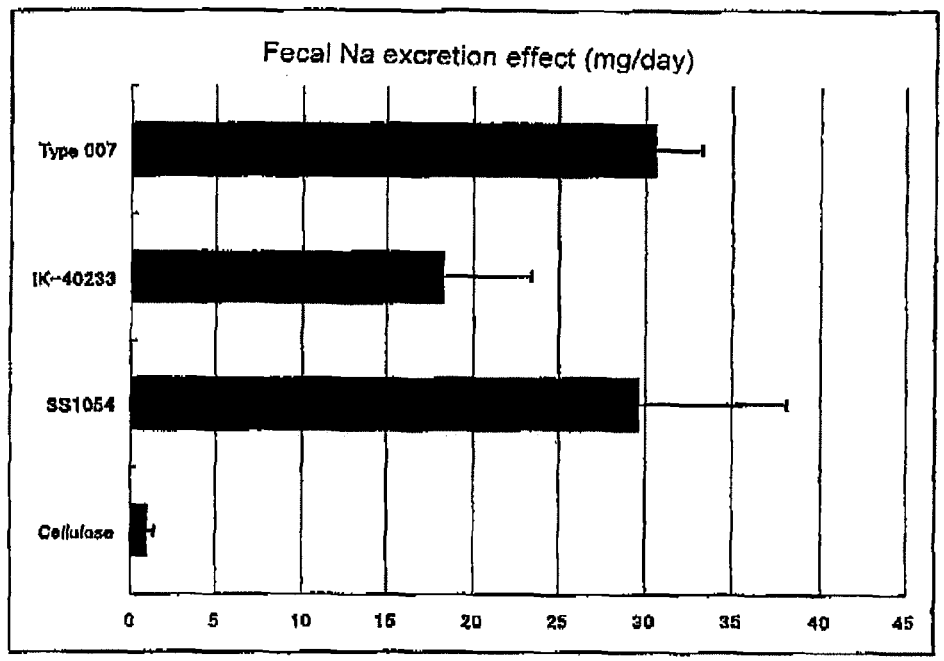
FIG. 1 (a) It is a figure showing results of fecal Na excretion effect of crosslinked sulfated cellulose calcium salts in <Test for Usefulness 1> as an average value±standard deviation. (b) It is a figure showing results of fecal Na excretion effect of a non-crosslinked sulfated cellulose calcium salt in <Referential Test> as an average value±standard deviation.
Figure 1:
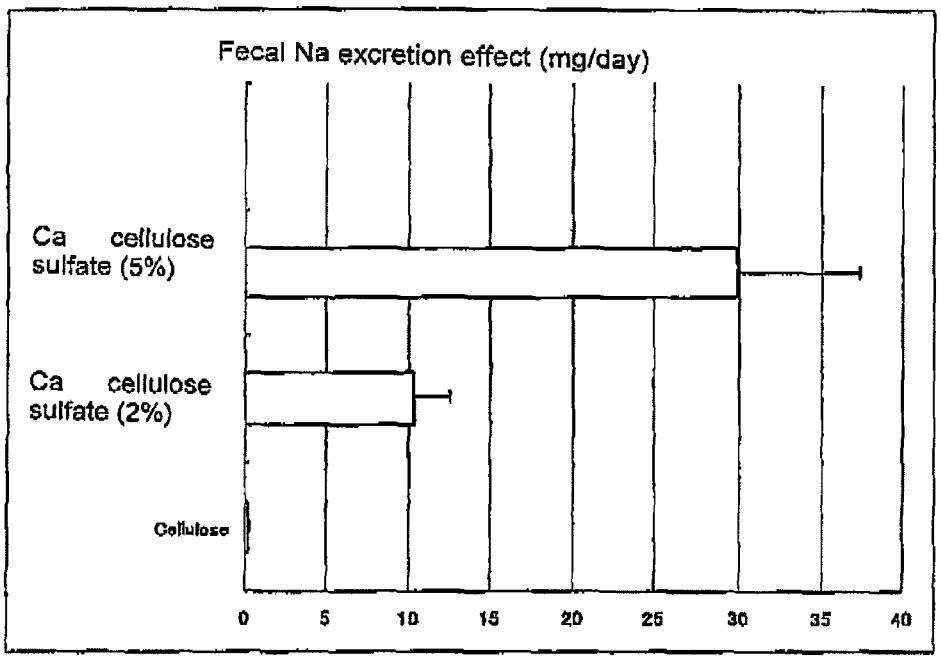

The metal salt of the crosslinked cellulose derivative of the invention is a metal salt wherein crosslinking and functional groups are introduced into cellulose. The crosslinked cellulose derivative is represented by the following formula (I) and degree of substitution of the hydroxyl group of glucose unit thereof by a functional group a is 1 or more.

R—O-A (I)

{in the formula (I), R represents a crosslinked cellulose residue and A represents a functional group having a cation-exchange ability.}

The degree of substitution can be calculated based on values obtained from elemental analysis as mentioned below.

Examples of the above functional group a having cation-exchange ability include groups having a carboxyl group, a sulfonic acid group, a phosphonic acid group, a phosphoric acid group, or the like, and it is preferable that the group is represented by the following formulae (II) to (V).

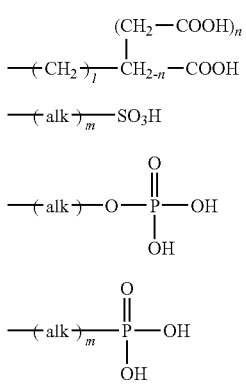

{in the formulae (II) to (V), alk represents an alkylene group having 1 to 6 carbon atoms, l represents an integer of 0 to 5, m represents 0 or 1, and n represents an integer of 0 to 2.}

The degree of substitution (n) of the functional group a can be determined based on the elemental analysis value (Y) of the element to be a target of the elemental analysis and its atomic weight (y) and atomic valence (m) according to the following equation.

$n=162Y \div \{y/m-(\text{value corresponding to (molecular weight of functional group a portion)}-(\text{weight of one hydrogen})Y\}$ The followings will specifically explain the calculation of the degree of substitution (n) in each formula.

The calculation of the degree of substitution in the case where the functional group a is the skeleton of the above formula (III) is herein explained. As one example, the calculation method is explained using the case of a calcium salt "—SO$_3$Ca$_{1/2}$" when m is 0 in the formula (III) as an example. First, the degree of substitution for the non-crosslinked cellulose is calculated considering the molecular weight of the glucose skeleton, which is one unit of the cellulose, to be 162. In the cellulose, in the case where one primary hydroxyl group is substituted by —SO$_3$Ca$_{1/2}$, i.e., the degree of substitution is 1, the molecular weight increases to be 261 by an increment of {(one sulfuric anhydride)+(Ca$_{1/2}$)−(hydrogen)}=99 and the elemental analysis value of S is calculated as follows:

32/261=about 12%.

When the degree of substitution is 2, the molecular weight increases to be 360 and thus the elemental analysis value of S is calculated as follows:

64/360=about 17.8%.

Namely, when the elemental analysis value of S is Y and the degree of substitution is n, $Y=32n \div (162+99n)$ and hence, $n=162Y \div (32-99Y)$.

Using the equation, the degree of substitution (n) can be calculated based on the elemental analysis value (Y) of S. For example, in the case where the elemental analysis value of S is 18%, the degree of substitution is about 2.1 when it is converted. In the case of the crosslinked cellulose, the value is calculated with considering the degree of crosslinking. For example, in the case where the structure of crosslinking is a 2-hydroxy-1,3-ether skeleton obtained from epichlorohydrin, the degree of substitution can be calculated with considering the molecular weights of the glucose skeleton and the crosslinked structure part and the degree of crosslinking.

For example, when the degree of crosslinking is 0.1 in terms of the definition to be mentioned below, since the molecular weight of the crosslinked structure part (C$_3$H$_4$O) is 56, the weight per glucose skeleton is (0.1×720×56÷240=) 16.8. Namely, the molecular weight per unit of the crosslinked cellulose is (162+16.8=) 178.8. When this value is applied to the equation in the case of the aforementioned cellulose, the degree of substitution (n) can be calculated based on the elemental analysis value (Y) of S as follows:

$n=178.8Y \div (32-99Y)$.

Then, the calculation of the degree of substitution is explained in the case where the functional group a is the skeleton of the above formula (II). As one example, in the case of the calcium salt "—CH$_2$—COOCa$_{1/2}$" wherein l is 0 and n is 0 in the formula (II), when one hydroxyl group of the glucose skeleton which is one unit of the cellulose is substituted, the molecular weight of the one unit is 162+78=240. When the elemental analysis value of Ca is Y and the degree of substitution is n, $Y=20n \div (162+78n)$ and the degree of substitution (n) can be calculated as follows:

$n=162Y \div (20-78Y)$ when the elemental analysis value of Ca (Y) is determined.

In the case where the functional group a is the skeleton represented by the above formula (IV) and alk is CH$_2$, the degree of substitution (n) can be calculated based one the elemental analysis value of P (Y). Namely, in the case of —CH$_2$O—P(O)(OCa$_{1/2}$)$_2$, when one hydroxyl group of the glucose skeleton which is one unit of the cellulose is substituted, the molecular weight of the one unit is 162+148=310.

$Y=31n \div (162+148n)$ and the degree of substitution (n) can be calculated as follows:

$n=162Y \div (31-148Y)$ when the elemental analysis value of P (Y) is determined.

In the case where the functional group a is the skeleton represented by the above formula (V), the degree of substitution can be calculated in the same manner as in the case where the functional group a is (IV), with adding the increment of the molecular weight of the alkylene group as in the case of the aforementioned skeleton (II).

The crosslinked cellulose derivative for use in the invention is a cellulose ether substituted by a functional group a having cation-exchange ability. The functional group a having cation-exchange ability may be used singly or as a combination of two or more thereof.

When there are two or more kinds of functional groups, substitution degree may be calculated from the elementary analysis value in the same manner as calculation method described above after calculating molecular weight of each functional group parts.

Preferable functional group a may include the following.

—CH$_2$—COOH   (II-1)

-continued

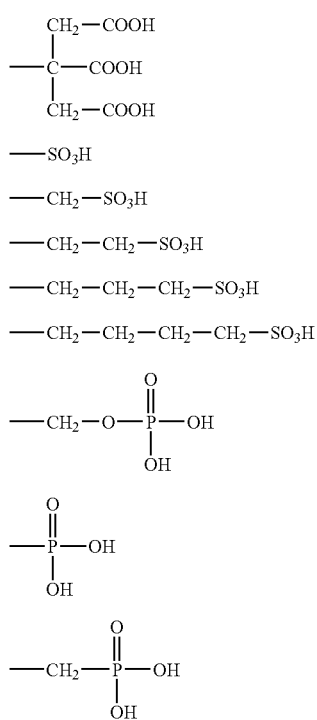

Moreover, as mentioned above, the crosslinked cellulose derivative (I) of the invention may have two or more functional group a having cation-exchange ability. For example, the cellulose derivatives composed of different types of the functional group having cation-exchange ability consisting of the combinations shown by the following (c-1) to (c-3) are preferable.

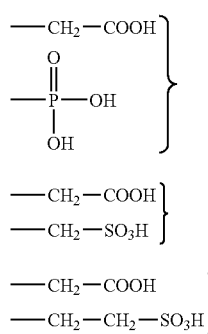

Moreover, with regard to the above group having a phosphonic acid group or a phosphoric acid group represented by the above formula (IV) or (V), at least one hydroxyl group may be present in the functional group. The hydroxyl group in the phosphonic acid group or the phosphoric acid group may be substituted by an alkoxy group, a phosphonic acid group, a thiol group, or the like according to needs. Specifically, the functional group a having cation-exchange ability of the invention also includes groups as shown in the following.

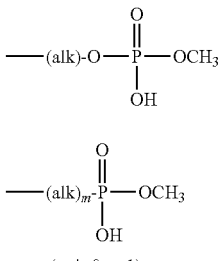

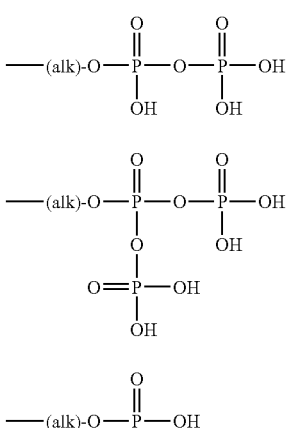

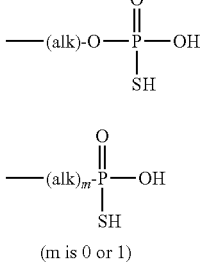

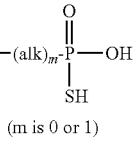

As the metal for forming the metal salt, an alkali metal such as potassium, an alkaline earth metal such as calcium or magnesium, or a metal such as iron can be used. Of these, potassium, calcium, magnesium and iron are preferable in view of ion exchange efficiency and from the viewpoint of acceptability even when they are released into the blood and the body.

The crosslinking in the crosslinked cellulose may be at any positions and may be either crosslinking within one cellulose or crosslinking between celluloses.

The degree of crosslinking of the metal salt of the crosslinked cellulose derivative of the invention is preferably 0.01 or more.

The degree of crosslinking can be calculated as follows.

A case where the cellulose for use in the reaction has a molecular weight of 39000 (average degree of polymerization: 240) and epichlorohydrin is used as a crosslinking agent is explained here as an example.

By epichlorohydrin, the crosslinked structure part is added as an increment to the cellulose sugar chain as shown in the following structural formula. The molecular weight of the increased part is 56.

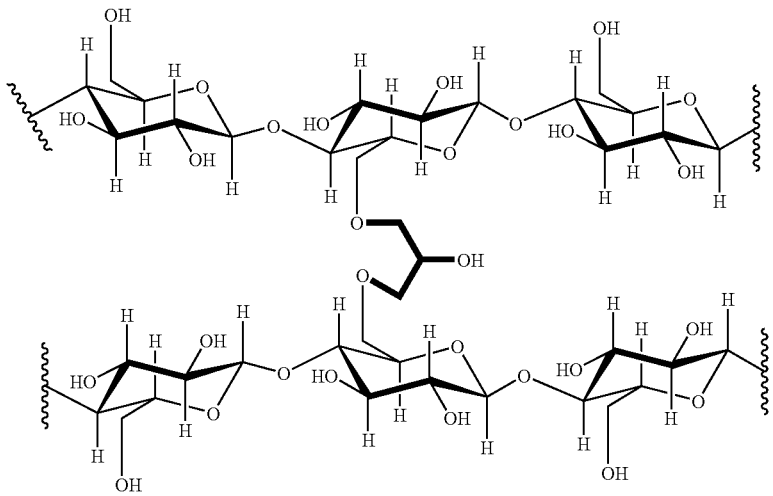

In the case where the weight of the crosslinked cellulose after crosslinking is increased by 4% from the charged amount of the cellulose before crosslinking as a value obtained after subtraction of a water content (analytical value), from the calculation based on the molecular weight of the cellulose of 39000:

39000×0.04=1560;

and based on the molecular weight of the increased molecular structure part of 56:

1560÷56=about 28, the crosslinked structure part is calculated to be about 28 mol. Namely, the ratio of crosslinking/cellulose is 28/1.

When this value is converted to a value per one hydroxyl group of the sugar, since one mol of the cellulose has 240 glucoses (average degree of polymerization) and three hydroxyl groups are present per glucose unit, the number of the hydroxyl groups per mol of the cellulose is calculated as follows:

240×3=720, and since the ratio of the crosslinked structure part is 28/1 as above, the value per one hydroxyl group is calculated as follows:

28/720=0.039.

Namely, the number of the crosslinked structure part per hydroxyl group is 0.039 and thus the value 0.039 can be defined as "degree of crosslinking" of the above crosslinked cellulose in the example.
[Production Method]

The metal salt of the invention can be produced by a production method comprising a crosslinking step and a functional group-introducing step. In view of the stability of the functional group, it is preferable to perform the functional group-introducing step after the crosslinking step.
{Cellulose}

As the cellulose, although known various celluloses can be used and their molecular weights are not particularly limited, crystalline cellulose (appears in Japanese Pharmacopoeia) wherein the degree of polymerization is homogenized and has a definite width is preferable.
{Crosslinking Step}

The crosslinking step can be achieved by reacting the cellulose with a crosslinking agent. The crosslinking agent for use in the invention includes aldehydes such as glyoxal, dialdehyde starch and polyacrolein; methylol compounds such as N-methylol-melamine and trimethylolmelamine; active vinyl compounds such as divinylsulfone; epoxy compounds such as epichlorohydrin, epibromohydrin, ethylene glycol diglycidyl ether, propylene glycol diglycidyl ether, glycerol polyglycidyl ether, pentaerythritol polyglycidyl ether, neopentyl glycol diglycidyl ether, 1,4-butanediol diglycidyl ether, 1,4-bis(2,3-epoxypropoxy)butane, 1,4-bisglycidoxybutane, 1,2-bis(2,3-epoxypropoxy)ethylene and 1,-(2,3-epoxypropyl)-2,3-epoxycyclohexane; polycarboxylic acids such as tartaric acid, citric acid, malic acid, maleic acid, fumalic acid, succinic acid, adipic acid, sebacic acid, aspartic acid, glutaric acid, tricarballylic acid, butanetetracarboxylic acid, polymaleic acid, polyacrylic acid and polyacrylic acid-maleic acid copolymers; diisocyanate compounds, oxyranylmethanol, N-ethylbis(2-chloroethyl)amine, methylvinyldiacetoxysilane, dimethyldiacetoxysilane, triglycidyltris(2-hydroxyethyl)isocyanurate, formaldehyde, glutaraldehyde, crotonaldehyde, 4,5-dihydroxyethyleneurea and divinylsulfone. An epoxy compound such as a halohydrin, a glycidyl ether, or an epoxyalkane is preferable. Epichlorohydrin is particularly preferable.

These crosslinking agents may be used in combination of two or more thereof.

The amount of the above crosslinking agent to be used is 0.1 to 500 parts by weight based on 100 parts by weight of the cellulose and it is preferable that 100 to 300 parts by weight based on 100 parts by weight of the cellulose is used. It is further preferable that the amount is 150 to 200 parts by weight. When the amount falls within the range, a sufficient crosslinking is obtained and unreacted matter does not remain, so that the case is useful.

In the invention, for the purpose of smooth progress of the crosslinking reaction with the above crosslinking agent, a crosslinking reaction catalyst can be suitably used according to the type of the crosslinking agent. In the case where the crosslinking agent is a polycarboxylic acid, examples of the crosslinking reaction catalyst include phosphoric acid compounds such as phosphoric acid, sodium hypophosphite, potassium dihydrogen phosphate and sodium phosphate, inorganic acids such as sulfuric acid and hydrochloric acid, sodium carbonate, sodium acetate, titanium compounds, and the like. Moreover, in the case where an epoxy compound is used as the crosslinking agent, basic compounds such as sodium hydroxide and potassium hydroxide, amines such as primary amines, secondary amines and tertiary amines, quaternary ammonium salts, imidazole compounds, alcohols, water, and the like are used.

The amount of the above crosslinking reaction catalyst to be used is 1 to 200 parts by weight based on 100 parts by weight of the above crosslinking agent and it is preferable 80 to 150 parts by weight based on 100 parts by weight of the above crosslinking agent is used Although the methods for crosslinking the above cellulose with the above crosslinking agent is not particularly limited, for example, the methods include a method described in JP-A-63-54160 and the like method. Specifically, there may be many methods such as a method through dry crosslinking wherein the cellulose is impregnated with an aqueous solution of the crosslinking agent followed by removing water and the product was dried at a high temperature and an aqueous solution crosslinking method wherein the above cellulose is crosslinked in an aqueous solution of the crosslinking agent. A two-layer crosslinking method wherein the crosslinking agent and the cellulose are vigorously stirred in an aqueous solution of a crosslinking reaction catalyst as a two-layer system to effect crosslinking is more preferable.

It is preferable that the degree of crosslinking is 0.01 or more as mentioned above. It is more preferable that the degree is 0.01 or more and 0.30 or less, and further preferable that the degree is 0.03 or more and 0.20 or less.

The control of the degree of crosslinking can be achieved by the ratio of the amount of a base or an acid to be added for activation of the functional group and the amount of the crosslinking agent to be added relative to the cellulose. Moreover, since it is a solid-liquid reaction, it is possible to control the degree by the type of the solvent to be used or by the ratio of solvents when two or more solvents are used. In order to control the degree of crosslinking within a preferable range, it is preferred to control the degree mainly by the ratio of the amount of a base or an acid to be added for activation of the functional group and the amount of the crosslinking agent to be added relative to the cellulose.

For example, in the case where the crosslinking agent is epichlorohydrin, since the hydroxyl group is a functional group, sodium hydroxide is used as the base. In the case where the ratio of epichlorohydrin to sodium hydroxide is constant, the degree of crosslinking increases as the ratio of epichlorohydrin to the cellulose increases. However, in the case where sodium hydroxide is large excess to the cellulose or the concentration of the aqueous solution of sodium hydroxide is high, there is a concern that the decomposition reaction of the cellulose may proceeds in parallel, and thus the degree of crosslinking is not necessarily improved.

Moreover, in the case where a polar solvent such as methanol or isopropanol is used in a large amount as the solvent to be used, although decomposition of the cellulose (decrease in molecular weight) proceeds and the degree of crosslinking increases, there is a possibility that decrease in recovery rate may occur.

As a result of extensive studies of the inventors, it is preferable that the ratio of epichlorohydrin to sodium hydroxide (in terms of mol), i.e., epichlorohydrin/sodium hydroxide is 1/2 to 1/4, and it is further preferable that the ratio is 1/2.3 to 1/3.2. When represented as a ratio thereof to the cellulose, cellulose/sodium hydroxide/epichlorohydrin is 1/6/3 to 1/20/5, and further preferably 1/7/3 to 1/16/5.

The solvent to be used includes three-phase such as n-heptane/methanol/water and n-heptane/isopropyl alcohol/water, two-phase such as an n-heptane/water system, and non-polar solvents and polar solvents (water alone or alcoholic ones), and n-heptane/water is further preferable.

Furthermore, by dividing the amount of the crosslinking agent, i.e., increasing the number of addition with small portions, the amount of the crosslinking agent which is not used in the crosslinking reaction can be reduced and the degree of crosslinking can be further increased. Moreover, the degree of crosslinking can be further increased by raising the stirring rate, changing the shape of the stirring blade, and adding baffles, and making reaction scale to be smaller, for example.

{Functional Group-Introducing Step}

As mentioned above, the functional group-introducing step is preferably performed after the crosslinking step.

In the case where the functional group-introducing step includes sulfation, the functional group-introducing step is more preferably performed after the crosslinking step. For example, in the case where the functional group a is the skeleton of the above formula (III), examples of a sulfation agent for introducing a sulfate group into the hydroxyl group of the cellulose include conc. sulfuric acid, fuming sulfuric acid, sulfuric anhydride, a sulfuric anhydride/DMF complex, a sulfuric anhydride/pyridine complex, a sulfuric anhydride/triethylamine complex, chlorosulfonic acid, and the like. A sulfuric anhydride/DMF complex is preferably used.

However, in the case where the functional group a is the skeleton of the above formula (II), in the case of using a known cellulose derivative, 6-hydroxyethylcellulose or 6-hydroxypropylcellulose as a starting material, the functional group-introducing step preferably contains functional group conversion (in this case, oxidation reaction) and the crosslinking step is preferably conducted after the functional group-introducing step.

The sulfated crosslinked cellulose is directly transformed into a metal salt with calcium chloride added beforehand after removing the unreacted crosslinking agent and its derivative together with the solvent. Alternatively, the metal salt can be obtained by adding an alcohol such as methanol or isopropanol and an inorganic salt and then vigorously stirring the whole. Moreover, after once producing the calcium salt, a metal salt can be obtained through a replacement reaction with an inorganic salt.

The metal salt of the crosslinked cellulose derivative represented by the formula (I) of the invention has such a high value of the degree of substitution of the functional group in the crosslinked cellulose derivative as 1 or more. It is preferable that the degree of substitution is 1.2 or more, it is more preferable that the degree is 1.4 or more, and it is further preferable that the degree is 1.5 or more. In order to control the degree of substitution to the above range, it is preferable to control the degree of crosslinking in the crosslinking step.

In the case where the functional group a is the skeleton of the above formula (II), when the starting material is known 6-hydroxyethylcellulose or 6-hydroxypropylcellulose, exceptionally, it is preferable that the degree of substitution is 0.8 or more, it is more preferable that the degree is 0.9 or more, and it is further preferable that the degree is 1.0 or more.

On the other hand, in the conventional sulfation method, it is not easy to obtain a preferable degree of substitution only by controlling the degree of crosslinking. In the following, a case where the functional group a is the skeleton of the above formula (III) is explained as an example.

In order to improve the degree of substitution of the sulfate group, it is suitable to increase the ratio of the sulfation agent to the crosslinked cellulose. However, in the case of a sulfuric anhydride/DMF complex which is the most powerful sulfation agent, since the solubility of sulfuric anhydride in DMF is a little less than 20%, there arises, of its own accord, a limitation on the concentration of the sulfation agent in the reaction system. As a result, there arises a limitation on improvement of the degree of substitution and particularly, it is difficult to increase the degree of substitution for the crosslinked cellulose having a high degree of crosslinking.

As a result of extensive studies on this point, the inventors have found that the concentration of the sulfuric anhydride relative to the crosslinked cellulose can be in creased about twice by directly adding sulfuric anhydride into the reaction system where the crosslinked cellulose is dispersed in DMF solvent even when the concentration thereof in DMF is constant, and one having a degree of substitution (1.5 or more) equal to or higher than the degree in the conventional case of the ratio of sulfuric anhydride/cellulose of 3/1 can be easily obtained even when the ratio is about 2/1. Namely, in order to obtain a high degree of substitution in the case of the crosslinked cellulose having a high degree of crosslinking, the purpose can be achieved by reacting the crosslinked cellulose in a high concentration state of sulfuric anhydride with reducing the amount of DMF relative to the crosslinked cellulose. In the case where the functional group a is the skeleton of the above formula (III), it is preferable that the degree of substitution is preferably 1.2 or more, it is more preferable that the degree is 1.4 or more, and it is further preferable that the degree is 1.5 or more.

Although the obtained metal salt of the crosslinked cellulose derivative may be used as it is, it may be used after further purification by precipitation with an alcohol, ion-exchange resin chromatography, gel filtration chromatography, or the like, if necessary.

The metal salt of the invention is useful as absorption inhibitors capable of oral administration to the human body. For example, the salt can be used as a sodium absorption inhibitor by transforming it into a salt with a metal other than sodium and the salt can be used as a potassium absorption inhibitor by transforming it into a salt with a metal other than potassium. This is seemed to be due to ion-exchange ability and there is an advantage that the effect is obtained by administration thereof in a small amount since the degree of substitution of the functional group a is high. Moreover, the salt can be used as a phosphorus absorption inhibitor. The metal salt of the invention is capable of suppressing the disorder of the digestive tract, which is considered to be attributable to crosslinking.

In addition, the salt is beneficially used as a water-holding agent.

EXAMPLES

Although the followings will describe the invention further in detail with reference to Examples, the invention is not limited thereto.

Referential Example

Production of Sulfated Cellulose Calcium Salt: CaCS-005 (Lot JK031215)

{First Stage: Sulfation Step}

In a 500 mL separable flask, 20.0 g (123.5 mmol in terms of glucose) of crystalline cellulose (manufactured by Asahi Kasei Corporation, trade name: CEOLUS PH-101) dried at 40° C. under vacuum was added, and the cellulose was then impregnated with 100 mL of DMF under stirring for 4 days.

The suspension was cooled to be 5° C. Then, while stirring, 371.8 g ($SO_3$: 0.929 mol) of a 20% sulfuric anhydride-DMF complex solution was gradually added dropwise from a dropping funnel connected to the separable flask with maintaining the inner temperature at 5° C. After completion of the dropwise addition, the temperature was adjusted at 16 to 17° C. in a constant temperature bath and the whole was stirred for 6 hours.

Then, 500 mL of isopropanol was added to the reaction solution. Precipitates from the reaction solution were filtrated off. The filtrated product was dissolved in 500 mL of water and calcium salt formation was carried out by adding 137.0 g of a saturated aqueous calcium chloride solution to precipitate a crude product, which was then filtrated off to obtain an objective product. The product was further washed with isopropanol (500 mL×twice). After removing isopropanol by a filtration operation, the product was dried in a vacuum drier to obtain 27.5 g of a sulfated cellulose calcium salt. Upon elemental analysis, the following was found: S; 16.0%, Ca; 12.4%, and the degree of substitution was 1.6.

{Second Stage: UF Membrane Ultrafiltration Step}

With 2000 mL of ion-exchange water, 25.05 g (78.18 mmol in terms of glucose) of sulfated cellulose calcium salt obtained in the first stage was dissolved under cooling.

Then, using an UF membrane (manufactured by Asahi Kasei Corporation: pencil-type module ACP-0013, nominal molecular weight cutoff: 13,000), ultrafiltration was carried out at a flow rate of 1.88 to 1.92 L/min. The raw solution was concentrated under circulation until the volume becomes 200 mL. The 200 mL portion was freeze-dried to finally obtain 17.68 g of a white powder.

Upon elemental analysis, the following was found: S; 18.3%, Ca; 12.4%, and the degree of substitution was 2.1.

Example

Production of Crosslinked Sulfated Cellulose Calcium Salt: CaCS-006 (Lot.IK031224)

{First Stage: Crosslinking Step}

In a 500 mL three-neck flask, 5.0 g (30.8 mmol in terms of glucose) of crystalline cellulose (manufactured by Asahi Kasei Corporation, trade name: CEOLUS PH-101) was added, and then a cooling tube and a dropping funnel were connected thereto. Separately, 8.6 g (206 mmol) of sodium hydroxide (96% grade) was dissolved in 50 mL of water. The prepared aqueous sodium hydroxide solution was transferred into the dropping funnel and was added to the crystalline cellulose. The whole was stirred at room temperature for 10 minutes to maintain the suspended state.

Then, 50 mL of n-heptane and 50 mL of methanol were added to the reaction system and the temperature was raised to be 50° C. Thereto, using the dropping funnel, a solution of 8.5 g (92 mmol) of epichlorohydrin dissolved in 50 mL of methanol was rapidly added dropwise to the suspension. While it was intended to achieve thorough mixing of the two layers, the mixture was stirred for 3 hours with maintaining the temperature of 50 to 60° C.

After cooling to be room temperature, conc. hydrochloric acid was gradually added with stirring to make the pH around 7.0. The mixture was once filtrated under reduced pressure and the filtrated product was washed with water and further washed with methanol. After removing methanol by a filtration operation, the product was thoroughly dried in a vacuum drier to obtain 6.1 g of a crosslinked cellulose. The degree of crosslinking was 0.174.

{Second Stage: Sulfation Step}

In a 500 mL separable flask, 4 g (0.0247 mol in terms of glucose) of the crosslinked cellulose obtained in the first stage was added, and the cellulose was then impregnated with 20 mL of DMF under stirring for 3 days. Thereafter, the suspension was cooled to be 5° C. Then, 74.12 g ($SO_3$: 0.185 mol) of a 20% sulfuric anhydride-DMF complex solution was gradually added dropwise from a dropping funnel connected to the separable flask with stirring. On this occasion, the reaction temperature was maintained at 5° C. After completion of the dropwise addition, the temperature was adjusted at 16 to 17° C. in a constant temperature bath and the whole was stirred for 24 hours.

Then, 100 mL of isopropanol was added to the reaction solution. Precipitates from the reaction solution were filtrated and separated. The filtrated product was added to 250 mL of water and the whole was stirred. Furthermore, 27.45 g of a saturated calcium chloride solution was added thereto, followed by stirring for 2 hours. Insoluble matter was filtrated off and the product was further washed with isopropanol (100 mL×twice). After removing isopropanol by a filtration operation, the product was thoroughly dried in a vacuum drier to obtain 8.09 g of a crosslinked sulfated cellulose calcium salt. Upon elemental analysis, the following was found: S; 17.6%, Ca; 10.8%, and the degree of substitution was 2.3.

Referential Example

Production of Crosslinked Sulfated Cellulose Calcium Salt: CaCS-007 (Lot.IK040113)

{First Stage: Crosslinking Step}

In a 500 mL three-neck flask, 16.0 g (99 mmol in terms of glucose) of crystalline cellulose (manufactured by Asahi Kasei Corporation, trade name: CEOLUS PH-101) was added, and then a cooling tube and a dropping funnel were connected thereto. Then, 300 ml, of n-heptane and 10 mL of isopropanol were added to the reaction system. After stirring for 30 minutes, separately, 32.0 g (768 mmol) of sodium hydroxide (96% grade) was dissolved in 100 mL of water. A half volume of the prepared aqueous sodium hydroxide solution was transferred into the dropping funnel and was added to the suspension, followed by stirring at room temperature for 1 hour.

Using the dropping funnel, 26.0 g (281 mmol) of epichlorohydrin was rapidly added dropwise to the suspension and the temperature was raised to be 50° C. In order to achieve thorough mixing of the two layers, the mixture was stirred for 3 hours with maintaining the temperature of 50 to 60° C. Then, the remaining sodium hydroxide solution was added dropwise, followed by stirring for 1.5 hours. After adding 26.0 g (281 mmol) of epichlorohydrin, the whole was further stirred for 2 hours.

After cooling to be room temperature, insoluble matter was filtrated off and the filtrated product was washed with water, 2N hydrochloric acid and water, successively, until pH of the washing liquid became around neutral. Further, it was washed with methanol. The product was dried in a vacuum drier to obtain 18.1 g of a crosslinked cellulose. The degree of crosslinking was 0.198.

{Second Stage: Sulfation Step}

In a 500 mL separable flask, 10 g (0.0617 mol in terms of glucose) of the crosslinked cellulose obtained in the first stage was added, and the cellulose was then impregnated with 50 mL of DMF under stirring for 3 days. Thereafter, the suspension was cooled to be 5° C. Then, with stirring, 206.04 g ($SO_3$: 0.463 mol) of an 18% sulfuric anhydride-DMF complex solution was gradually added dropwise from a dropping funnel connected to the separable flask. On this occasion, the reaction temperature was maintained at 5° C. After completion of the dropwise addition, the temperature was adjusted at 16 to 17° C. in a constant temperature bath and the whole was stirred for 24 hours.

Then, 250 ml, of isopropanol was added to the reaction solution. Precipitates from the reaction solution were filtrated and separated. The filtrated product was added to 625 mL of water and the whole was stirred. Furthermore, 68.60 g of a saturated aqueous calcium chloride solution was added thereto, followed by stirring for 2 hours. Insoluble matter was filtrated off and the product was further washed with isopropanol (100 mL×twice). After removing isopropanol by a filtration operation, the product was thoroughly dried in a vacuum drier to obtain 13.7 g of a crosslinked sulfated cellulose calcium salt. Upon elemental analysis, the following was found: S; 7.40%, Ca; 5.38%, and the degree of substitution was 0.58.

Example

Production of Crosslinked Sulfated Cellulose Calcium Salt: Lot.IK-40223)

{First Stage: Crosslinking Step}

In a 3 L three-neck flask, 80.0 g (0.494 mol in terms of glucose) of crystalline cellulose (manufactured by Asahi Kasei Corporation, trade name: CEOLUS PH-101) was added, and the cellulose was then suspended in 800 mL of MeOH and 800 mL of n-hexane. A cooling tube, a stirring blade (with a stirring motor) and a dropping funnel were connected thereto and stirring was performed. Separately, 140.0 g (3.36 mol) of sodium hydroxide (96% grade) was dissolved in 1600 mL of water. The prepared aqueous sodium hydroxide solution was transferred into the dropping funnel and was added to the suspension. The mixture was stirred at room temperature for 30 minutes to maintain the suspended state.

Then, the temperature was raised to be 50° C. Thereto, using the dropping funnel, a solution of 138.8 g (1.5 mol) of epichlorohydrin dissolved in 200 mL of methanol was added dropwise to the suspension. In order to achieve thorough mixing of the two layers, the mixture was stirred for 3 hours with maintaining the temperature of 50 to 60° C.

After cooling to be room temperature, the mixture was washed with water, 2N hydrochloric acid and water, successively, until pH of the washing liquid became around 7.0.

The mixture was filtrated under reduced pressure and the filtrated product was washed with methanol. After removing methanol by a filtration operation, the product was dried in a vacuum drier to obtain 84.4 g of a crosslinked cellulose. The degree of crosslinking was 0.053.

{Second Stage: Sulfation Step}

In a 500 mL separable flask, 40 g (0.247 mol in terms of glucose) of the crosslinked cellulose obtained in the first stage was added, and the cellulose was then impregnated with 200 mL of DMF under stirring for 3 days. Thereafter, the suspension was cooled to be 5° C. Then, with stirring, 900 g ($SO_3$: 2.025 mol) of an 18% sulfuric anhydride-DMF complex solution was gradually added dropwise from a dropping funnel connected to the separable flask. On this occasion, the reaction temperature was maintained at 5° C. After completion of the dropwise addition, the temperature was adjusted to be 16 to 17° C. in a constant temperature bath and the whole was stirred all day and night.

Then, 1000 mL of isopropanol was added to the reaction solution. Precipitates from the reaction solution were filtrated and separated. The filtrated product was dissolved in 1000 mL of water and calcium salt formation was carried out by adding 274.5 g of a saturated aqueous calcium chloride solution to precipitate a crude product, which was then filtrated and separated to obtain an objective product. The product was further washed with isopropanol (1000 mL×twice). After removing isopropanol by a filtration operation, the product was thoroughly dried in a vacuum drier to obtain 76.8 g of a crosslinked sulfated cellulose calcium salt. Upon elemental analysis, the following was found: S; 16.8%, Ca; 12.8%, and the degree of substitution was 1.9.

Example

Production of Crosslinked Sulfated Cellulose Calcium Salt: Lot.SS-1054

{First Stage: Crosslinking Step}

In a 3 L three-neck flask, 80.0 g (0.494 mol in terms of glucose) of crystalline cellulose (manufactured by Asahi Kasei Corporation, trade name: CEOLUS PH-101) was added, and then a cooling tube, a stirring blade (with a stirring motor) and a dropping funnel were connected thereto. Then, 800 mL of methanol and 800 mL of n-hexane were added thereto to form a suspension. Separately, 144.0 g (3.457 mol) of sodium hydroxide (96% grade) was dissolved in 800 mL of water under ice cooling. The prepared aqueous sodium hydroxide solution was transferred into the dropping funnel and was added to the suspension. The mixture was stirred at room temperature for 60 minutes to maintain the suspended state.

Then, the reaction system was heated to be 50° C. Thereto, using the dropping funnel, a solution of 159.9 g (1.728 mol) of epichlorohydrin dissolved in 200 mL of methanol was rapidly added dropwise to the suspension. In order to achieve thorough mixing of the two layers, the mixture was stirred for 6 hours with maintaining the temperature of 50 to 60° C.

After cooling to be room temperature, it was continued to stir the mixture for another 20 hours and then the mixture was transferred into a 5 L beaker, followed by standing for 4 hours. The supernatant was removed by decantation and the residue was suspended with water and then filtrated under reduced pressure. The filtrated product was again suspended with water and, with stirring, conc. hydrochloric acid was gradually added to make the pH around 7.0. The mixture was once filtrated under reduced pressure and the filtrated product was washed with water and further washed with methanol. After removing methanol by a filtration operation, the product was thoroughly dried in a vacuum drier to obtain 80.8 g of a crosslinked cellulose. The degree of crosslinking was less than 0.01.

{Second Stage: Sulfation Step}

In a 2 L three-neck flask, 30 g (0.18 mol in terms of glucose) of the crosslinked cellulose obtained in the first stage was added, and then 150 mL of DMF was added thereto, followed by stirring at room temperature for 21 hours. The suspension was cooled to be 5° C. Then, with stirring, 721.0 g (0.871 mol) of a sulfuric anhydride-DMF complex solution (18.5% grade) was gradually added dropwise from a dropping funnel connected to the separable flask. On this occasion, the reaction temperature was maintained at 5±5° C. After completion of the dropwise addition, the temperature was raised to be room temperature and the whole was stirred for 24 hours.

Then, filtration under pressure was performed using 1000 mL of isopropanol as washing liquid. After the filtrated product was dissolved in 750 mL of water, 198.0 g (0.555 mol) of a separately prepared aqueous calcium chloride solution (31.1%) was added thereto. Thereto, with stirring, 1000 mL of isopropanol was added to precipitate crystals, followed by standing for 60 minutes. The supernatant was removed by decantation and the residue was suspended with isopropanol and then filtrated under reduced pressure. The filtrated product was further washed with isopropanol. After removing isopropanol by a filtration operation, the product was thoroughly dried in a vacuum drier to obtain 79.8 g of a crosslinked sulfated cellulose calcium salt. Upon elemental analysis, the following was found: S; 17.8%, Ca; 12.4%, and the degree of substitution was 2.0.

Example

Production of Crosslinked Sulfated Cellulose Calcium Salt: Lot.Type-007

{First Stage: Crosslinking Step}

In a 3 L three-neck flask, 80.0 g (0.494 mol in terms of glucose) of crystalline cellulose (manufactured by Asahi Kasei Corporation, trade name: CEOLUS PH-101) was added, and then a cooling tube, a stirring blade (with a stirring motor) and a dropping funnel were connected thereto. Separately, 329.2 g (7.901 mol) of sodium hydroxide (96% grade) was dissolved in 800 mL of water. The prepared aqueous sodium hydroxide solution was transferred into the dropping funnel and was added to the crystalline cellulose. The mixture was stirred at room temperature for 30 minutes to maintain the suspended state.

Then, the reaction system was heated to be 50° C. Thereto, using the dropping funnel, a solution of 228.4 g (2.469 mol) of epichlorohydrin dissolved in 1,600 mL of n-heptane was rapidly added dropwise to the suspension. In order to achieve thorough mixing of the two layers, the mixture was stirred for 3 hours with maintaining the temperature of 50 to 60° C.

After cooling to be room temperature, with stirring, conc. hydrochloric acid was gradually added to make the pH of the aqueous layer around 7.0. The mixture was once filtrated under reduced pressure and the filtrated product was washed with water and further washed with methanol. After removing methanol by a filtration operation, the product was thoroughly dried in a vacuum drier to obtain 94.9 g of a crosslinked cellulose. From the chart showing no crystallinity obtained by X-ray diffraction of the compound, it was confirmed that crosslinking had proceeded. The degree of crosslinking was 0.180.

{Second Stage: Sulfation Step}

In a 500 mL three-neck flask, 25 g (0.130 mol in terms of glucose) of the crosslinked cellulose obtained in the first stage was added together with 34.3 g (0.309 mol) of calcium chloride, and then 300 mL of DMF was added thereto, followed by stirring at room temperature for 24 hours. The suspension was cooled to be 5° C. Then, with stirring, 28.9 mL (0.694 mol) of sulfuric anhydride was gradually added dropwise from a dropping funnel connected to the three-neck flask. On this occasion, the reaction temperature was maintained at 20±5° C. After completion of the dropwise addition, the temperature was raised to room temperature and the whole was stirred for 24 hours.

Then, filtration under reduced pressure was performed using 1000 mL of isopropanol as washing liquid. The filtrated product was washed with water (1000 mL×three times). The filtrated product was further washed with methanol (500 mL×twice). After removing methanol by a filtration operation, the product was thoroughly dried in a vacuum drier to obtain 48.0 g of a crosslinked sulfated cellulose calcium salt.

Upon elemental analysis, the following was found: S; 16.7%, Ca; 9.7%, and the degree of substitution was 1.9.

Example

Production of Crosslinked Sulfated Cellulose Potassium Salt: Lot.KCS01-001

{Second Stage: Sulfation Step}

In a 2 L flask equipped with a stirrer, a thermometer and a dropping funnel, 50.0 g (0.260 mol in terms of glucose) of the crosslinked cellulose produced in the same manner as in the production method of {First Stage: Crosslinking Step} in Example Lot.Type-007 and 68.5 g (0.617 mol) of calcium chloride were added. After changing to an atmosphere under a nitrogen stream, 800 mL of DMF was added with ice cooling to form a suspension. After cooling to be 5° C., the suspension was warmed to be room temperature and stirred under a nitrogen stream for 24 hours. The suspension was cooled to be −20° C. Then, with stirring, 59.0 mL (1.42 mol) of sulfuric anhydride was gradually added dropwise from a dropping funnel connected to the separable flask. On this occasion, the reaction temperature was maintained at −20 to 0° C. After completion of the dropwise addition, the temperature was raised to be 20±5° C. and the whole was stirred for 24 hours.

Then, 1000 mL of methanol was added to the reaction system and then filtration under pressure was performed. After washing with 1000 mL of isopropanol, the filtrated product was added to 800 mL of water and stirred to form a suspension. An aqueous potassium hydroxide solution was gradually added to the suspension to make the pH of the aqueous layer around 7.0. After filtration under pressure, 400 g of a 25% aqueous potassium chloride solution was added to the obtained filtrated product and the stirring state was maintained for 2 hours. After filtration under reduced pressure, 400 g of a 25% aqueous potassium chloride solution was added to the again obtained filtrated product and the stirring state was maintained for 2 hours. Filtration under reduced pressure was performed and the filtrated product was further washed with water and acetone and then thoroughly dried in a vacuum drier. As a result, 109.8 g of a crosslinked sulfated cellulose potassium salt was obtained. Upon elemental analysis, the following was found: S; 15.7%, K; 20.2%, Ca; 0.45%, and the degree of substitution was 1.89.

Production Example

Production of Crosslinked Alkyl Sulfated Cellulose Calcium Salt

Example

Crosslinked Propyl Sulfated Cellulose Calcium Salt: Lot.ME13-138

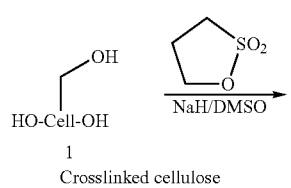
1
Crosslinked cellulose

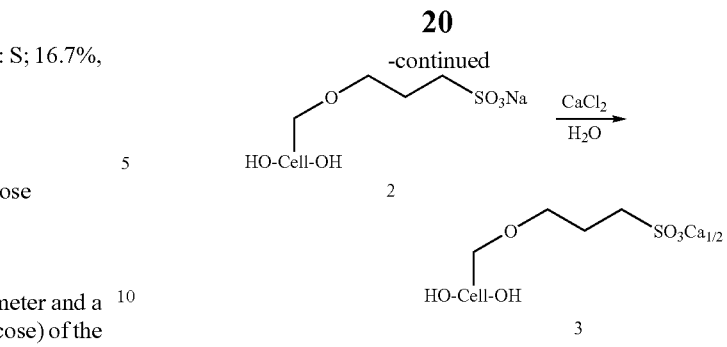

{First Stage: Crosslinking Step}
{Second Stage: Sulfation Step}

After washing 7.8 g (0.20 mol) of NaH with 100 mL of hexane, it was suspended in 200 mL of DMSO and replacement with argon was performed. To the solution, 30 g of the crosslinked cellulose [Compound 1 in the above chemical reaction formula; a crosslinked cellulose (0.156 mol in terms of glucose) produced in the same manner as in the production method of {First Stage: Crosslinking Step} in Example Lot.Type-007] was added, followed by stirring at 50° C. for 1 hour. Furthermore, a DMSO (25 mL) solution of 23.7 g (0.19 mol) of 1,3-propanesultone was added dropwise and the whole was stirred at 50° C. for 16 hours. The reaction solution was added to 700 mL of cold methanol. The obtained crystals (above Compound 2) were filtrated under reduced pressure and washed with methanol (100 mL×3), followed by drying under vacuum at 70° C. for 2 hours.

The yield was 51.4 g. Upon elemental analysis, the following was found: Na; 6.1%, S; 8.9%, and the degree of substitution was 0.9.

To an aqueous solution (350 mL) of 117 g (0.80 mol) of $CaCl_2 \cdot 2H_2O$, 50 g of Compound 2 (0.149 mol in terms of glucose) was added, followed by stirring at 50° C. for 12 hours. The reaction solution was centrifuged (3000 rpm/20 minutes/4° C.). The obtained residue was washed with 250 mL of water and centrifuged (each operation was conducted three times). The product was added to 450 mL of methanol and stirred at room temperature for 30 minutes to obtain Compound 3. The obtained Compound 3 was subjected to filtration under reduced pressure and washed with methanol (100 mL×2), followed by drying under vacuum at 70° C. for 4 hours.

The yield was 47.3 g. Upon elemental analysis, the following was found: Ca; 5.5%, S; 8.7%, and the degree of substitution was 0.8.

Example

Sulfation of Crosslinked Propyl Sulfated Cellulose Calcium Salt Lot.ME13-138: Lot.ME13-135, ME13-141

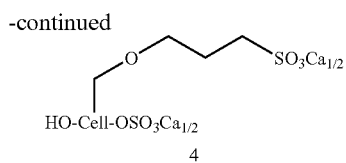

Into 15 mL of anhydrous DMF, 2.0 g of the above Compound 3 (6.00 mmol in terms of glucose) and 0.98 g (8.8 mmol) of $CaCl_2$ were suspended, and then, under replacement with argon, the whole was stirred at room temperature for 12 hours. To the suspension, 3.1 g (20 mmol) of a sulfuric anhydride-DMF complex was added, followed by stirring at room temperature for 1 hour and at 50° C. for 10 hours. To the reaction solution, 30 mL of isopropanol was added, and the resulting crystals were filtrated under reduced pressure. To the obtained residue, 30 mL of water was added and neutralized with an aqueous calcium hydroxide solution. The resulting solution was centrifuged (3000 rpm/30 min./4° C.). After adding 50 mL of water to the residue and stirring, centrifugation was performed under the same conditions. The washing operation with water was again performed, followed by centrifugation. After suspending the obtained Compound 4 in 100 mL of methanol, the suspension was filtrated under reduced pressure and drying under vacuum was performed at 60° C. for 10 hours. (ME13-135)

The yield was 1.9 g. Upon elemental analysis, the following was found: Ca; 8.5%, S; 13%, and the degree of substitution was 1.7.

Moreover, in the same manner, 49 g of Compound 4 was obtained from 45 g of Compound 3. (ME13-141)

Upon elemental analysis, the following was found: Ca; 10.7%, S; 12.6%, and the degree of substitution was 1.6.

Example

Production of Crosslinked Bispropyl Sulfated Calcium Salt: Lot.ME13-147

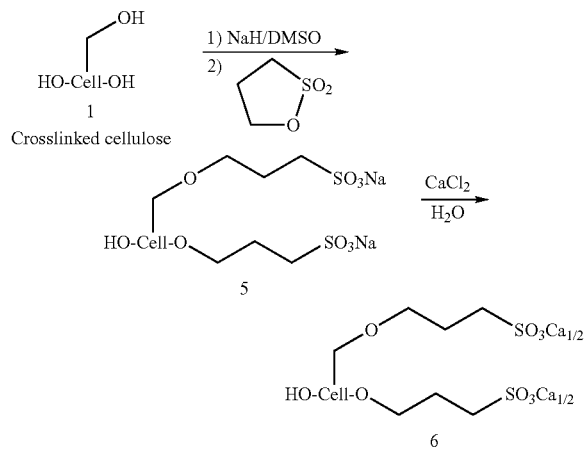

After washing 17.6 g (0.44 mol) of NaH with 120 mL of hexane, it was suspended into 200 mL of DMSO and replacement with argon was performed. To the solution, 30 g of Compound 1; a crosslinked cellulose (0.156 mol in terms of glucose) produced in the same manner as in the production method of {First Stage: Crosslinking Step} in Example Lot.Type-007 was added, followed by stirring at 50° C. for 1 hour. Furthermore, a DMSO (50 mL) solution of 53.8 g (0.44 mol) of 1,3-propanesultone was added dropwise and the whole was stirred at 50° C. for 24 hours. The reaction solution was added to 400 mL of cold methanol. The obtained crystals (above Compound 5) were filtrated under reduced pressure and washed with methanol (250 mL×2) and diethyl ether (200 mL), followed by drying under vacuum at 70° C. for 1 hour. (ME13-146)

The yield was 73.9 g. Upon elemental analysis, the following was found: Na; 9.1%, S; 12%, and the degree of substitution was 1.6.

To an aqueous solution (300 mL) of 229 g (1.5 mol) of $CaCl_2.2H_2O$, 70 g of Compound 5 (0.146 mol in terms of glucose) was added, followed by stirring at 50° C. for 12 hours. The reaction solution was centrifuged (3000 rpm/20 minutes/4° C.). The obtained residue was washed with water (250 mL) and centrifuged (each operation was conducted three times), and the product was added to 400 mL of methanol. The obtained Compound 6 was subjected to filtration under reduced pressure, washed with methanol (100 mL×2), and dried under vacuum at 70° C. for 4 hours. (ME13-147)

The yield was 46.8 g. Upon elemental analysis, the following was found: Ca; 7.2%, S; 11%, and the degree of substitution was 1.3.

Example

Production of Crosslinked 6-Hydroxycarbonylmethyloxycellulose Calcium Salt

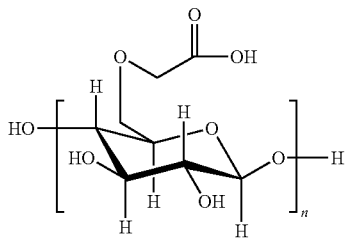

{First Step; Production of 6-Hydroxycarbonylmethyloxycellulose}

In a 1 L round-bottom flask equipped with a stirrer, a thermometer and a dropping funnel, 10.2 g (0.0495 mol in terms of glucose) of hydroxyethylcellulose (manufactured by Wako Pure Chemical Industries, Ltd.) was dispersed into 700 mL of ion-exchange water. Thereto, 28 mg of TEMPO and 260 mg of sodium bromide were added, followed by stirring at room temperature. Thereto, 77 g of a 5% aqueous sodium hypochlorite solution (manufactured by Wako Pure Chemical Industries, Ltd.) was added.

Since the pH of the reaction solution was gradually lowered, a 0.2M aqueous sodium hydroxide solution was suitably added to maintain the pH at about 10.5. After about 1 hour, when the situation that the pH was not so much changed was confirmed, 10 mL of the 0.2M aqueous sodium hydroxide solution was added, followed by stirring at room temperature overnight. Next morning, the pH of the reaction solution whose pH had been 9.9 was lowered to be pH 1.8 by the use of 1N hydrochloric acid.

The reaction solution was transferred to a 3 L beaker and 1400 mL of 2-propanol was added thereto to effect crystallization. After standing for two nights, the supernatant was decanted and the remaining matter was subjected to suction filtration. The filtrated product was washed with ethanol and dried under reduced pressure at 60° C. overnight to obtain 10.8 g of a white powder.

Upon IR measurement, a strong peak derived from C=O stretching originated from a carboxyl group was confirmed at 1730 cm$^{-1}$.

{Second Step; Crosslinking of 6-Hydroxycarbonylmethyloxycellulose}

In a 1 L three-neck flask, 10.8 g (0.049 mol in terms of glucose) of 6-hydroxycarbonylmethyloxycellulose obtained in the first step was added, and then a cooling tube, a stirring blade (with a stirring motor) and a dropping funnel were connected thereto. Separately, 4.2 g (0.1 mol) of sodium hydroxide (96% grade) was dissolved in 200 mL of water. The prepared aqueous sodium hydroxide solution was added to the crystalline cellulose. The mixture was stirred at room temperature for 30 minutes.

Then, the reaction system was heated to 50° C. Thereto, using the dropping funnel, a solution of 12 g (0.13 mol) of epichlorohydrin dissolved in 160 mL of n-heptane was rapidly added dropwise to the suspension. In order to achieve thorough mixing of the two layers, the mixture was stirred for 3 hours with maintaining the temperature of 50 to 60° C.

After cooling to be room temperature, conc. hydrochloric acid was gradually added to make the pH of the aqueous layer around 7.0 with stirring. The mixture was once filtrated under reduced pressure and the filtrated product was washed with water and further washed with methanol. After removing methanol by a filtration operation, the product was dried at 60° C. in a vacuum drier overnight. As a result, 12.8 g of 6-hydroxycarbonylmethyloxycellulose was obtained. From the chart showing no crystallinity obtained by X-ray diffraction of the compound, it was confirmed that crosslinking had proceeded.

{Third Step; Calcium Salt Formation of Crosslinked 6-Hydroxycarbonylmethyloxycellulose}

Into 100 mL of pure water, 12 g (0.05 mol in terms of glucose) of the white powder was dissolved, and then 30 g of calcium chloride and 4 g of calcium hydroxide were added thereto. After stirring for 3 hours, the suspension was allowed to stand overnight. Using 1N hydrochloric acid, the pH of the suspension was lowered from 11.5 to 7.5 to effect neutralization. The suspension was subjected to suction filtration and the filtrated product was washed with ethanol. The filtrated product was dried at 60° C. overnight to obtain 12 g of a white fine powder.

Upon elemental analysis, the following was found: Ca; 7.2 and the degree of substitution was 1.0. Moreover, upon IR measurement, a strong peak derived from C=O stretching originated from a carboxyl group was confirmed at 1730 cm$^{-1}$.

<Test for Usefulness 1>

{Influence of Crosslinked sulfated cellulose (Ca) on Electrolyte Excretion into Feces of Normal Rat}

[Method]

As animals, SD male rats purchased from Charles River Japan Inc. were used. The rats were kept with fasting overnight and then habituated for 3 days to a powder feed under restricted feeding using a cellulose feed wherein 1% of a purified feed (casein 25.0%, α-corn starch 51.5%, soybean oil 6.0%, sucrose 5.0%, AIN76 mineral mix 3.5%, AIN76 vitamin mix 1.0%, and cellulose 8.0%) was replaced with NaCl and 5% thereof was replaced with Cellulose. Thereafter, body weights of the animals were measured and the animals were grouped using the feed intake and body weight as indices. Namely, a control group wherein the cellulose feed was ingested and test substance (SS1054, IK-40223, Type007) groups wherein a feed obtained by replacing 1% of the purified feed cellulose with NaCl and 5% thereof by each of the test substances was ingested were provided. After keeping the rats of each group kept with fasting overnight, they were kept with each test feed under restricted feeding (20 g/day) for 4 days. On third day of the keeping with the test feed, feces were collected from 17 o'clock for 48 hours. During the test period, the rats of each group were allowed to drink distilled water freely. After drying the collected feces in a dryer at 50° C. for 5 days, the dry weights were determined. Thereafter, they were incinerated into ash (500° C., 36 hours or more) and suspended with distilled water, followed by centrifugation. Then Na concentration and K concentration of the supernatant were measured by the ion electrode method to determine respective contents. With regard to P, after solubilization treatment with conc. nitric acid, the concentration in the solution was measured by the enzyme method to determine the content.

[Results]

Figure 2:
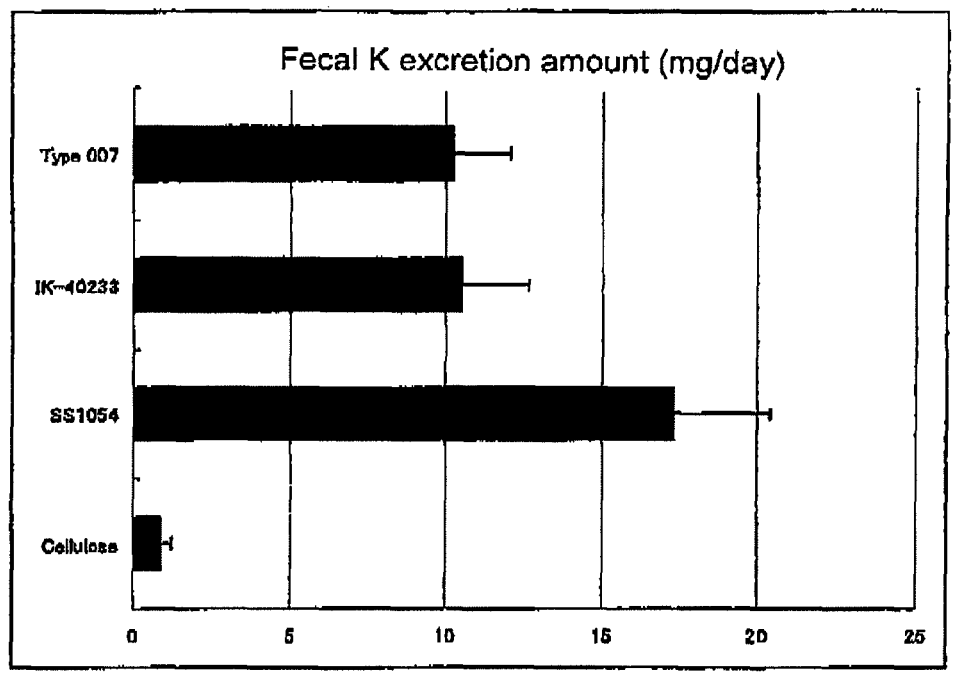
FIG. 2 It is a figure showing results of fecal K excretion effect of crosslinked sulfated cellulose calcium salts in <Test for Usefulness 1> as an average value±standard deviation.
Figure 3:
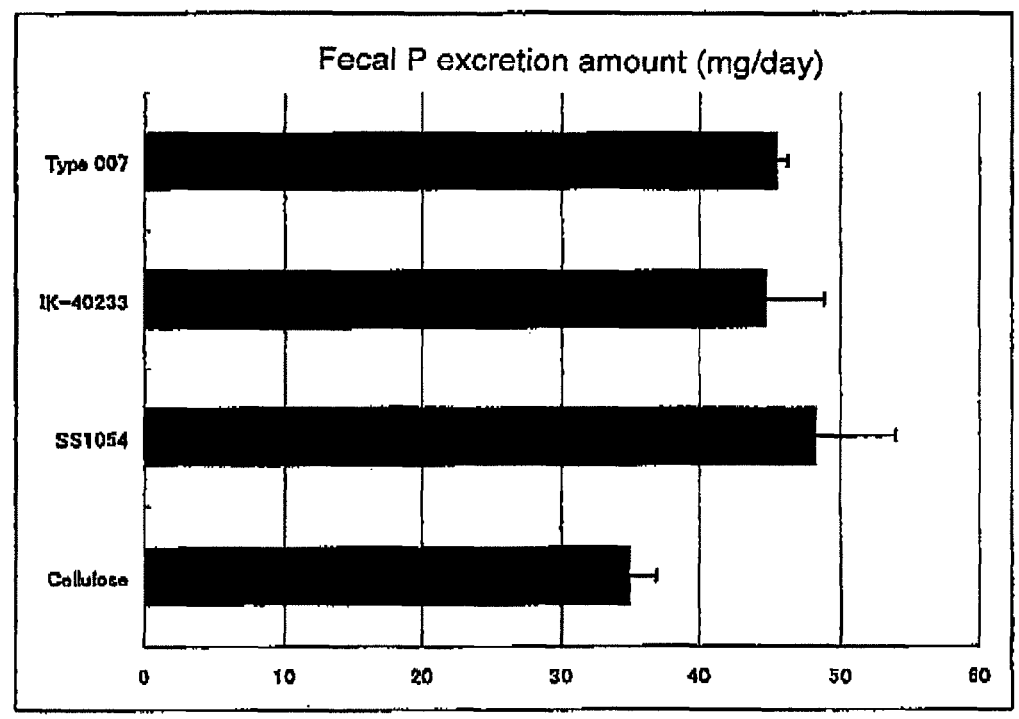
FIG. 3 It is a figure showing results of fecal P excretion effect of crosslinked sulfated cellulose calcium salts in <Test for Usefulness 1> as an average value±standard deviation.

The fecal electrolyte excretion amounts (mg/day, average value±standard deviation) in the cellulose group (n=4) were 1.0±0.4 (Na), 0.9±0.3 (K) and 34.9±2.0 (P), respectively. The fecal electrolyte excretion amounts (mg/day) in the SS-1054 group (n=4) were 29.6±8.5 (Na), 17.3±3.1 (K) and 48.3±5.7 (P), respectively. The fecal electrolyte excretion amounts (mg/day) in the IK-40233 group (n=4) were 18.2±5.2 (Na), 10.5±2.2 (K) and 44.8±4.2 (P), respectively. The fecal electrolyte excretion amounts (mg/day) in the Type007 group (n=4) were 30.6±2.7 (Na), 10.2±1.9 (K) and 45.4±0.9 (P), respectively. Thus, increase in fecal excretion of various electrolytes was observed in the test substance groups. These results are graphed and shown in FIG. 1A and FIG. 2 to FIG. 3.

Moreover, decrease in the electrolyte excretion in urine was observed corresponding to the increase in fecal excretion. With regard to CaCS006 used in <Test for Usefulness 6> to be mentioned below, a similar effect was observed.

<Referential Test>

{Influence of Sulfated Cellulose (Ca) on Electrolyte Excretion into Feces of Normal Rat}

(Production of Sulfated Cellulose Calcium Salt)

In a 5 L-volume beaker containing 1 L of distilled water (D.W.), 50 g of a sulfated cellulose sodium salt (manufactured by Acros Co. USA) was added, followed by stirring to achieve complete dissolution. Thereafter, 300 mL of an aqueous solution of 93 g of calcium chloride dihydrate (manufactured by Katayama Chemical Ltd.) was charged thereto, followed by stirring for 30 minutes. Thereto, 1 L of isopropyl alcohol was added, and the mixture was further stirred for 1 hour and then allowed to stand overnight. The supernatant was removed by decantation and the residue was further centrifuged to obtain precipitates. The precipitates were again suspended into 1 L of isopropyl alcohol, and the mixture was further stirred for 30 minutes and then allowed to stand overnight. The supernatant was removed by decantation and the residue was further centrifuged to obtain precipitates. The precipitates were dried under reduced pressure to obtain 44 g of a sulfated cellulose calcium salt as a white powder.

[Method]

As animals, 9 week-old Wister male rats (Charles River Japan Inc.) were used. The rats were kept with fasting overnight, then transferred to individual metabolism cages, and habituated for 3 days to a powder feed under restricted feeding (20 g/rat/day) using a cellulose feed (casein 20% (w/w, the same is applied hereinafter), α-corn starch 59.5%, soybean oil 5%, sucrose 5.0%, AIN-76 vitamin mix 1%, AIN-76 mineral mix 3.5%, common salt 1%, and cellulose 5%).

Thereafter, body weights of the animals were measured and the animals were grouped using the feed intake and body weight as indices during the habituation period (n=5/group). Namely, a cellulose group wherein the cellulose feed was ingested and a 2% sulfated cellulose calcium salt group and a 5% sulfated cellulose calcium salt group wherein a feed obtained by replacing 40% of the cellulose in the cellulose feed with the sulfated cellulose calcium salt or a feed obtained by replacing all of the cellulose in the cellulose feed with the sulfated cellulose calcium salt was ingested, respectively were provided.

After keeping the rats of each group with fasting overnight, they were kept with each test feed under restricted feeding (20 g/rat/day) for 2 days. On second day of the keeping with the test feed, urine and feces were collected from 7 p.m. for 24 hours. During the test period, the rats of each group were allowed to drink distilled water freely. After subjecting the collected feces to drying treatment at 70° C. for 4 days and determining the dry weights, they were incinerated into ash (500° C., 36 hours) and sodium was measured by atomic absorption method. With regard to the collected urine, assuming that the specific gravity was 1.0 from the weight difference of the urine-collecting cup, sodium in urine was measured by the ion electrode method.

[Results]

The fecal sodium excretion in each group was shown in FIG. 1(b). In FIG. 1(b), the sulfated cellulose calcium salt was described as "Ca cellulose sulfate".

The fecal sodium excretion was 10.4±2.2 mg/day in the 2% sulfated cellulose calcium salt group and 29.9±7.5 mg/day in the 5% sulfated cellulose calcium salt group, as compared with 0.2±0.1 mg/day in the cellulose group. Thus, dose-dependant increase in fecal sodium excretion induced by the sulfated cellulose calcium salt ingestion was confirmed.

On the other hand, the sodium excretion in urine was found to be 65.3±4.5 mg/day in the 2% sulfated cellulose calcium salt group and 40.3±3.4 mg/day in the 5% sulfated cellulose calcium salt group, as compared with 89.6±6.5 mg/day in the cellulose group. Thus, dose-dependant decrease in sodium excretion in urine induced by the calcium sulfate cellulose ingestion was confirmed.

<Test for Usefulness 2>

[Method]

The test was carried out in the same manner as in the above <Test for Usefulness 1>. A feed obtained by mixing a purified feed (raw materials per 950 g: casein 200 g, α-corn starch 595 g, soybean oil 50 g, sucrose 50 g, AIN76 mineral mix 35 g, AIN76 vitamin mix 10 g, and NaCl 10 g) and ME13-147 in a ratio of 9:1 was orally ingested (20 g/day) for 2 days and feces were collected on the second day of the keeping with the test feed.

[Results]

As compared with the Cellulose group (0.8±0.1 (Na), 0.5±0.1 (K)), increase in fecal excretion was observed for each electrolyte, e.g., the ME13-147 group (4.3±1.3 (Na), 4.2±1.7 (K)).

<Test for Usefulness 3>

[Method]

The test was carried out in the same manner as in the above <Test for Usefulness 1>. A purified feed (casein 20%, α-corn starch 59.5 g, soybean oil 5%, sucrose 5%, AIN76 mineral mix 3.5%, AIN76 vitamin mix 1%, NaCl 1.0%, and Cellulose or ME13-141 5.0%) was orally ingested (20 g/day) for 4 days and feces were collected on the third day and the fourth day of the keeping with the test feed.

[Results]

As compared with the Cellulose group (0.5±0.1 (Na), 0.4±0.1 (K)), increase in fecal excretion was observed for each electrolyte, e.g., the ME13-141 group (23±6 (Na), 6±2 (K)).

<Test for Usefulness 4>

[Method]

The test was carried out in the same manner as in the above <Test for Usefulness 1>. A purified feed (casein 20%, α-corn starch 59.5 g, soybean oil 5%, sucrose 5%, AIN76 mineral mix 3.5%, AIN76 vitamin mix 1%, NaCl 1.0%, and Cellulose or KCS01-001 5.0%) was orally ingested (20 g/day) for 4 days and feces were collected on the third day and the fourth day of the keeping with the test feed.

[Results]

As compared with the Cellulose group (0.3±0.0 (Na), 0.6±0.1 (K)), increase in fecal excretion was observed for each electrolyte in the KCS01-001 group (47±7 (Na), 34±5 (K)).

<Test for Usefulness 5>

{Influence of Crosslinked Sulfated Cellulose (Ca) on Digestive Tract of Normal Mouse}

[Method]

As animals, 7 to 9 week-old CBA male mice purchased from Charles River Japan Inc. were used and they were grouped using the body weight as an index. The mice of each group were allowed to freely ingest a test feed obtained by replacing 10% of a commercially available powdered feed (Oriental Yeast Co., Ltd., Powder CRF1) with either of a cellulose (powder, Nakarai Tesque, Inc.) or a test substance (SS1054, IK-40223, Type007) for 1 week. After completion of the test feed ingestion, one or more feces was collected from each mouse, a fecal occult blood test by the chemical method using a slide (fecal occult blood slide Shionogi II, Shionogi & Co., Ltd.) was carried out, and the results were rated at scores from 0 (no change) to 5 (dark) depending on the degree of color tone change.

[Results]

In the cellulose group, the appearance and condition of the feces were normal in all cases and the fecal occult blood test score was 0.5±0.0 (n=8, average value±standard deviation). In the SS-1054 group, the symptom of the digestive tract became such worse that attachment of the blood was observed in the vicinity of the anus in six cases among eight cases and, on and after the fourth day from the start of the test, constitutional symptom was became such severe that obvious decrease in feed intake was observed. In the IK-40223 group, no decrease in feed intake was observed during the test period of 7 days and the fecal occult blood test score was 1.5±0.8 (8). In the Type007 group, the feces of every mouse was normal and the fecal occult blood test score was 0.5±0.3 (10).

<Test for Usefulness 6>

{Influence of Crosslinked Sulfated Cellulose (Ca) on Digestive Tract of Normal Mouse}

[Method]

As animals, 9 week-old CBA male mice purchased from Charles River Japan Inc. were used and they were grouped using the body weight as an index. The mice of each group were allowed to freely ingest a test feed obtained by replacing 10% of a commercially available powdered feed (Oriental Yeast Co., Ltd., Powder CRF1) with either of a cellulose (powder, Nakarai Tesque, Inc.) or a test substance (CaCS005, CaCS006, CaCS007) for 6 days. After completion of the test feed ingestion, one or more feces was collected from each mouse, a fecal occult blood test by the chemical method using a slide (fecal occult blood slide Shionogi II, Shionogi & Co., Ltd.) was carried out, and the results were rated at scores from 0 (no change) to 5 (dark) depending on the degree of color tone change.

[Results]

In the cellulose group, the appearance and condition of the feces were normal in all cases and the fecal occult blood test score was 0.3±0.3 (n=5, average value±standard deviation) at the time when the test was completed. In the CaCS005 group, on and after the second day from the start of the test, a fecal occult blood response (score 1.8±0.5 (n=4)) was observed. Thereafter, in the animals of the CaCS005 group, decrease in feed intake was remarkable, there were observed some animals which became such severe that mucous and bloody stool was observed, and the arms and legs were whitened due to anemia in all cases. The fecal occult blood test score was 3.3±1.3 (n=4) at the time when the test was completed. The appearance and condition of the feces during the test period in the CaCS006 group and the CACS007 group were almost normal and the fecal occult blood test scores at the time when the test was completed were 0.5±0.0 (n=3, on the fifth day from the start of the test) in the CaCS006 group and 0.2±0.3 (n=3) in the CaCS007 group, so that the disorder in the digestive tract was obviously alleviated. No anemia was observed.

<Test for Usefulness 7>

[Method]

In the same manner as in the above <Test for Usefulness 5>, mice were allowed to freely ingest a test feed obtained by mixing a commercially available powdered feed (Oriental Yeast Co., Ltd., Powder CRF1) with a test substance (KCS01-001) in a ratio of 10% for one week.

[Results]

In the cellulose group, the appearance and condition of the feces were normal in all cases and the fecal occult blood test score was 0.5 to 1 (n=8). Also, in the KCS01-001 group, the appearance and condition of the feces were normal in all cases and the fecal occult blood test score was 0.5 to 1 (n=8) and thus a minor response was observed in the fecal occult blood test.

<Test for Usefulness 8>

[Method]

In the same manner as in the above <Test for Usefulness 5>, mice were allowed to freely ingest a test feed obtained by mixing a commercially available powdered feed (Oriental Yeast Co., Ltd., Powder CRF1) with a test substance (ME13-147, ME13-141) in a ratio of 10% for one week.

[Results]

In the cases where either test substance was ingested, no bloody stool was observed and also and a minor response was observed in the fecal occult blood test.

The invention claimed is:

1. A metal salt of a crosslinked cellulose represented by the following formula (I), wherein the degree of substitution of the hydroxyl group of glucose unit of the crosslinked cellulose by a functional group "A" is 1 or more:

$$R\text{—}O\text{—}A \qquad (I)$$

wherein R represents a crosslinked cellulose residue and A represents —$SO_3H$, wherein the degree of crosslinking is 0.174-0.3, both inclusive, and the degree of substitution n is calculated by the following equation:

$n$=(the molecular weight of one unit of crosslinked cellulose)*$Y$÷[$y$/$m$−((molecular weight of $SO_3H$)−(atomic weight of one hydrogen))*$Y$]

Y: the elemental analysis value of sulfur,
y: the atomic weight of sulfur,
m: the atomic valence of sulfur.

* * * * *